(12) United States Patent
Honma et al.

(10) Patent No.: US 6,569,903 B2
(45) Date of Patent: May 27, 2003

(54) OPHTHALMIC COMPOSITIONS

(75) Inventors: Yoichi Honma, Osaka (JP); Yukie Akagi, Osaka (JP); Nobutoshi Matsushita, Osaka (JP); Ichiro Hirotsu, Osaka (JP)

(73) Assignee: Rohto Pharmaceutical Co., Ltd. (JP)

( * ) Notice: Subject to any disclaimer, the term of this patent is extended or adjusted under 35 U.S.C. 154(b) by 0 days.

(21) Appl. No.: 09/890,899

(22) PCT Filed: Dec. 6, 2000

(86) PCT No.: PCT/JP00/08623

§ 371 (c)(1),
(2), (4) Date: Nov. 14, 2001

(87) PCT Pub. No.: WO01/41806

PCT Pub. Date: Jun. 14, 2001

(65) Prior Publication Data

US 2003/0008805 A1 Jan. 9, 2003

(30) Foreign Application Priority Data

Dec. 7, 1999 (JP) ............................................ 11-348048

(51) Int. Cl.⁷ ............................................ A61K 31/135
(52) U.S. Cl. ...................... 514/649; 514/652; 514/912
(58) Field of Search ................................ 514/649, 652, 514/912

(56) References Cited

U.S. PATENT DOCUMENTS 5,314,916 A      5/1994   York et al.
6,066,675 A  *   5/2000   Wen et al. ................... 514/649

FOREIGN PATENT DOCUMENTS

EP        0234854        2/1987
JP          52727        2/1989
WO      WO 96/04911      2/1996

OTHER PUBLICATIONS

Bromberg (1981) Invest. Ophtalmol. Vis. Sci. 20(1):110–116.
Danjo et al. (1997) New Ophtalmol. 14(11):1631–1636 (w/English Translation).
Ogawa (1993) Diagnosis and Treatment of Ocular Surface pp 24–30 (w/English Translation).
Petounis et al. (1989) Int. Ophtalmol. 13(1–2):75–80.

* cited by examiner

Primary Examiner—Zohreh Fay
(74) Attorney, Agent, or Firm—Fish & Richardson P.C.

(57) ABSTRACT

Ophthalmic compositions having negligible side effects on the heart can be obtained by using as the active ingredient an adrenergic β receptor agonist having a high selectivity toward adrenergic $\beta_2$ receptor. These compositions are usable as preventives or therapeutics for xerophthalmic disorder and keratoconjunctival disorder.

5 Claims, No Drawings

OPHTHALMIC COMPOSITIONS

This application is a 371 of PCT/JP00/08623 filed Dec. 6, 2000.

TECHNICAL FIELD

The present invention relates to an ophthalmic composition containing a selective adrenergic $\beta_2$ receptor agonist.

BACKGROUND ART

Tear film covers the ocular surface, consisting of the cornea and conjunctiva, to keep it moisturized and protect it from drying. At the same time, tears function as a transparent optical transmissive liquid that maintains the corneal surface flat and smooth for the clear viewing of images. Tears also contain a large number of ingredients such as antibodies that prevent infections by viruses, bacteria, etc. Furthermore, tears play a role in washing away foreign substances which happen to get into eyes as well as cellular wastes derived from the cornea and conjunctiva. In addition, tears serve as a supply source of oxygen, moisture and nutrients for the cornea, which is an avascular tissue, and actively contribute to the healing of eye wounds, serving as a source of various biologically active substances at the time of keratoconjunctival disorders (corneal and conjunctival injuries) (Ocular Surface no Shindan to Chiryou (Diagnosis and Treatment of Ocular Surface), 24–30 (1993)).

Methods known in the art for treating hypolacrimia, xerophthalmia, dry eye, keratoconjunctivitis sicca, and such, which are all accompanied with the aberrant tear secretion, involve externally supplementing natural tears in shortage with artificial tears, and prolonging the retention time of artificial tears in the conjunctival sac by combining the artificial tears with viscous materials and such. However, since the actual tears contain a variety of biologically active substances as described above which contribute to the homeostasis and functional restoration (healing of injuries) of ocular surface, the mere moisture replenishment with artificial tears and such is insufficient to act as substitute for the role of natural tears. Therefore, there has been a strong demand for drugs capable of quantitatively as well as qualitatively improving tear secretion (Atarashii Ganka (New Ophthalmology), 14, 1631–1636 (1997)).

Promotion of tear secretion by isoproterenol, a $\beta$ adrenergic receptor agonist, has been hitherto reported (Invest. Ophthalmol. Vis. Sci., 20, 110–116 (1981)). There exist two subtypes, $\beta_1$ and $\beta_2$, for the $\beta$ adrenergic receptors, $\beta_1$ being distributed mainly in the heart while $\beta_2$ is predominantly in the smooth and skeletal muscles. Since isoproterenol is a nonselective $\beta$ adrenergic receptor agonist which strongly acts on either $\beta_1$ or $\beta_2$ receptor, it acts on the heart, wherein the $\beta_1$ adrenergic receptor is abundant, often causing unfavorable side effects on the cardiovascular system, specifically inducing an increase in the heart rate and an enhancement of heart contractile force. Thus, administration of a nonselective $\beta$ adrenergic receptor agonist as a bronchodilator is often accompanied with side effects on the cardiovascular system. In light of its unfavorable side effects, isoproterenol, a tear secretion promoting agent, is difficult to use as a tear secretion improving agent.

Research aiming at reducing side effects and prolonging actions of $\beta$ adrenergic receptor agonists, focusing on the organ distribution of $\beta$ adrenergic receptor subtypes, has been ongoing. In recent years, drugs having a high selectivity to the $\beta_2$ adrenergic receptor with a low cardiac distribution, so-called selective $\beta_2$ adrenergic receptor agonists, have been developed among $\beta$ adrenergic receptor agonists. Since selective $\beta_2$ adrenergic receptor agonists directly act on $\beta_2$ adrenergic receptors in smooth muscles to dilate bronchus and blood vessels, and also relax uterus, and such, they are applied to the treatment of bronchial asthma, threatened abortion, etc. Drugs of this type are inert to cardiovascular systems in therapeutic doses, expressing no action to increase the heart rate and/or to enhance heart contractile force. However, there has been no report on actions of these selective $\beta_2$ adrenergic receptor agonists concerning the promotion of tear secretion, increase in protein concentration in tears, and the treatment of keratoconjunctival and xerophthalmic disorders.

DISCLOSURE OF THE INVENTION

It is an object of this invention to provide an ophthalmic composition with as low side effects on the heart as possible, more specifically, to provide a composition whose side effects on the heart are sufficiently suppressed and which is capable of promoting tear secretion. It is another object of this invention to provide a composition which is able to increase protein concentration secreted in tears.

Present inventors proposed that compounds that promote tear secretion and, moreover promote secretion of tear proteins, which function as biologically active substance in particular, would be useful for the treatment of xerophthalmic and keratoconjunctival disorders. Further, they have selected the $\beta$ adrenergic receptor agonist as candidate compound for drugs having the activity to promote tear secretion. To develop drugs to improve tear secretion targeting the $\beta$ adrenergic receptor, it is necessary to avoid side effects thereof on the heart. To solve these problems, present inventors paid attention to the distribution of $\beta$ adrenergic receptor subtypes in the lacrimal gland and heart. That is, more $\beta_1$ adrenergic receptors are distributed in the heart, while more $\beta_2$ adrenergic receptors in the lacrimal gland. Present inventors proposed to avoid side effects on the heart by utilizing the difference in $\beta$ adrenergic receptor subtypes in both tissues, and discovered that agents that improve tear secretion with less side effect on the heart could be provided by utilizing $\beta$ adrenergic receptor agonists having a high selectivity for the $\beta_2$ adrenergic receptor. Furthermore, they confirmed that $\beta_2$ adrenergic receptor agonists, in addition to promoting tear secretion level, acted to increase the protein concentration in tears, thereby accomplishing this invention. That is, the present invention relates to the following compositions, methods for improving tear secretion using such compounds, and methods for suppressing their side effects.

[1] A composition for treating and/or preventing diseases due to xerophthalmic and/or keratoconjunctival disorders, said composition comprising a selective $\beta_2$ adrenergic receptor agonist as an active ingredient.

[2] A composition for treating and/or preventing at least one disease selected from the group consisting of keratoconjunctivitis sicca, lacrimal hyposecretion, xerophthalmia, dry eye, age-related xerophthalmia, Stevens-Johnson syndrome, corneal epithelial disorder, corneal epithelial detachment and keratoconjunctival ulcer, said composition comprising a selective $\beta_2$ adrenergic receptor agonist as an active ingredient.

[3] The composition of [1] or [2], wherein the selectivity of the selective $\beta_2$ adrenergic receptor agonist to the $\beta_2$ adrenergic receptor is not less than ten times the selectivity to the $\beta_2$ adrenergic receptor of isoproterenol.

[4] The composition of any one of [1] to [3], wherein said selective $\beta_2$ adrenergic receptor agonist is one or more compounds selected from the group consisting of clenbuterol, fenoterol, procaterol, salbutamol, salmeterol, hexoprenaline, pirbuterol, mabuterol, bambuterol, formoterol, meluadrine, tulobuterol, levosalbutamol, and their salts.

[5] The composition of any one of [1] to [4], wherein said composition is a pharmaceutical preparation formulated for oral administration.

[6] The composition of any one of [1] to [4], wherein said composition is a pharmaceutical preparation formulated for parenteral administration.

[7] The composition of [6], wherein said pharmaceutical preparation formulated for parenteral administration is an eye drop (an ophthalmic solution) or an eye ointment (ophthalmic ointment).

[8] The composition of [7], wherein said composition comprises 0.00001 to 5 w/v % of a selective $\beta_2$ adrenergic receptor agonist in the whole of the eye drop or eye ointment.

[9] A method for improving tear secretion, said method comprising administering a selective $\beta_2$ adrenergic receptor agonist.

[10] The method of [9], wherein said improved tear secretion involves an increase in tear secretion level and/or protein concentration in tears.

[11] A method for reducing the side effects of a tear secretion improving agent comprising a $\beta$ adrenergic receptor agonist as an active ingredient, said method in which a compound having a stimulatory activity selective to the $\beta_2$ adrenergic receptor is used as a $\beta$ adrenergic receptor agonist.

[12] A composition for improving tear secretion comprising a selective $\beta_2$ adrenergic receptor agonist as an active ingredient.

The present invention provides an ophthalmic composition containing a selective $\beta_2$ adrenergic receptor agonist as an active ingredient. In this invention, an "ophthalmic composition" means a medical composition which is administered solely for the purpose of treating and preventing disorders of the eye. Therefore, for example, in addition to pharmaceutical preparations for local administration, such as eye drops, eye ointment, etc., other types of preparations, administered for the purpose of treating and preventing disorders of the eye, are also included in the ophthalmic composition of this invention, even though they are indirectly administered to eyes, as in the case of oral pharmaceutical preparations. $\beta_2$ adrenergic receptor agonists used in this invention are compounds which selectively act on the $\beta_2$ adrenergic receptor, that is, selective $\beta_2$ adrenergic receptor agonists. Selectivity means that, even at a drug dose at which negligible side effects on the heart are detectable, a stimulatory activity of the drug specific for the $\beta_2$ adrenergic receptor, such as broncodilating activity and/or lung function improving activity, can be observed. Selective $\beta_2$ adrenergic receptor agonist is highly specific to the $\beta_2$ adrenergic receptor, as indicated by the ratio of stimulating activities thereof for the $\beta_1$ and $\beta_2$ adrenergic receptors used as index. From that reason, selective $\beta_2$ adrenergic receptor agonists exert no significant side effects on the cardiovascular system, such as the increase in the heart rate and heart excitation.

Selectivity of a drug to the $\beta_2$ adrenergic receptor can be represented using as an index the ratio between the pharmacological activity of the drug directed by the $\beta_1$ adrenergic receptor and that directed by the $\beta_2$ adrenergic receptor. Pharmacological activity directed by the $\beta_1$ adrenergic receptor is represented by, for example, the concentration of a drug needed to show an increase in the heart rate (EC50) in an excised atrium. On the other hand, pharmacological activity directed by the $\beta_2$ adrenergic receptor is represented by, for example, the concentration of a drug needed to show a relaxation of smooth muscle (EC50) in an excised trachea or uterus. Thus, specificity to the $\beta_2$ adrenergic receptor can be represented by a value obtained by dividing the former EC50 ($\beta_1$) by the latter EC50 ($\beta_2$). A larger value indicates a higher specificity of a compound to the $\beta_2$ adrenergic receptor. In this invention, a selective $\beta_2$ adrenergic receptor agonist means a compound having a higher specificity to the $\beta_2$ adrenergic receptor than the specificity to the receptor of isoproterenol. Excised organs used for comparing pharmacological activity are generally obtained from guinea pigs.

More preferably, the selective $\beta_2$ adrenergic receptor agonist of the present invention is a compound having specificity to $\beta_2$ adrenergic receptor which is at least 10 times, preferably 100 times, more preferably 1000 times higher than that of isoproterenol. Examples of relative specificities of selective $\beta_2$ adrenergic receptor agonists to the tracheal smooth muscle are as follows: fenoterol's specificity is about 20 times higher than that of isoproterenol; salbutamol's is about 30 times higher; pirbuterol's is about 260 times higher; formoterol's is about 630 times higher; procaterol's is about 2000 times higher; and clenbuterol's is about 7000 times higher than that of isoproternol. Herein, isoproterenol as a standard compound for comparison can take the form of a hydrochloride or sulfate.

Alternatively, a selective $\beta_2$ adrenergic receptor agonist which binds with a $\beta_2$ adrenergic receptor with affinity not less than 10 times that with which it binds with a $\beta_1$ adrenergic receptor can be utilized as a tear secretion improving agent of this invention in a therapeutically effective dose thereof. Affinity of a selective $\beta_2$ adrenergic receptor agonist to a $\beta_2$ adrenergic receptor is preferably not less than 100 times, more preferably not less than 1000 times that to a $\beta_1$ adrenergic receptor. Binding affinity to a $\beta_1$ or $\beta_2$ adrenergic receptor can be confirmed by conventional methods known in the art. For example, the affinity can be measured by a competitive binding assay using the cardiac muscle tissue to test a $\beta_1$ adrenergic receptor, and the lung tissue to test a $\beta_2$ adrenergic receptor.

Since the composition of this invention comprises an agonist that selectively acts on the $\beta_2$ adrenergic receptor, it does not act on the heart, an organ with little distribution of the $\beta_2$ adrenergic receptor. For that reason, the composition can effectively avoid side effects on the heart, in spite of the fact that it comprises a $\beta$ adrenergic receptor agonist as an active ingredient. As a result, side effects thereof on the heart are negligible in doses which improving effects on tear secretion can be expected.

Examples of $\beta_2$ adrenergic receptor agonists used in this invention are selective $\beta_2$ adrenergic receptor agonists or salts thereof such as clenbuterol, fenoterol, procaterol, salbutamol, salmeterol, hexoprenaline, pirbuterol, mabuterol, banbuterol, formoterol, meluadrine, tulobuterol, levosalbutamol, etc. Furthermore, derivatives of these selective $\beta_2$ adrenergic receptor agonists and salts thereof may be used. In this invention, salts are referred to as medicinally acceptable non-toxic salts. Examples of these salts are hydrochlorides, sulfates, hydrobromides, valerates, citrates, gluconates, succinates, tartarates, fumarates, etc. All of these drugs have selectively high affinities to the $\beta_2$ adrenergic receptor as compared with the $\beta_1$ adrenergic receptor. Selective $\beta_2$ adrenergic receptor agonists are classified by the structural modification into the short acting type, having a bronchial dilation action duration time of less than 6 h, and the long acting type, having a bronchial dilation action duration time not less than 6 h. In this invention, either type can be used. Among them, from the aspect of prolonged protection of the corneal surface, the long acting type is more preferable. The long acting type includes pirbuterol, fenoterol, procaterol, clenbuterol, mabuterol, salmeterol, formoterol, tulobuterol, etc. In this invention, selective $\beta_2$ adrenergic receptor agonists can be used singly or in combination, i.e. a plurality of these compounds.

A variety of proteins such as IgG, IgA, EGF, lactoferrin, FGF, lysozyme, fibronectin, etc. are secreted into tears. All of these selective $\beta_2$ adrenergic receptor agonists have the action to promote tear secretion. These selective $\beta_2$ adrenergic receptor agonists are physiologically as well as pharmacologically acceptable compounds that act as a promoter for the secretion of tear proteins. Therefore, with the combination of these compounds, the promoting effects on tear secretion and the elevated secretion of a variety of proteins, which have repairing functions on keratoconjunctival tissues, etc., can be expected. Specifically, with the combination of these compounds, the improved function to prevent infection accompanied with an increase in IgG and IgA secretion, to stimulate repair of keratoconjunctival tissues and promote proliferation of corneal epithelial cells and differentiation of corneal epithelium, accompanied with the increase in the secretion of biologically active substances such as EGF, lactoferrin, FGF, lysozyme, etc., can be expected. Therefore, these compounds can be used for the treatment and/or prevention of disorders accompanied with keratoconjunctival injuries.

By this invention, an ophthalmic composition or tear secretion improving agent comprising a selective $\beta_2$ adrenergic receptor agonist as an active ingredient is provided. The composition according to this invention has the activity to enhance the secretion level of tears and/or promote the secretion of proteins into tears. In a preferred embodiment, the composition of this invention has the action to promote not only tear secretion level but also protein secretion into tears.

The composition of this invention can be used as a tear secretion improving agent based on its tear secretion improving action. In this invention, a tear secretion improving agent means a pharmaceutical preparation with improving effects on the decrease in the tear secretion level and qualitative aberration of tears. Alternatively, a tear secretion improving agent of this invention can be referred to as a pharmaceutical preparation with at least either one of the effects: to promote tear secretion level and protein secretion into tears.

The tear secretion improving agent according to this invention is effective in improving conditions resulting from a decrease in tear secretion and qualitative aberration of tears. Decrease in tear secretion and qualitative aberration of tears are accompanied with subjective symptoms such as dry sensation (dry eye), foreign substance sensation, burning sensation, congestion, ophthalmalgia, eyestrain, asthenopia, itching eye, uncomfortable feeling of eyes, difficulty to open eyes. Therefore, the tear secretion improving agent of this invention is effective in improving these uncomfortable symptoms.

Alternatively, the composition of this invention can be utilized for the purpose of, for example, treating and/or preventing the following symptoms:

xerophthalmic disorder,
keratoconjunctival disorder,
keratoconjunctivitis sicca,
lacrimal hyposecretion,
xerophthalmia,
dry eye,
age-related xerophthalmia,
Stevens-Johnson syndrome,
corneal epithelial disorder,
corneal epithelial detachment and
keratoconjunctival ulcer.

Furthermore, this invention relates to the use of selective $\beta_2$ adrenergic receptor agonists in the preparation of ophthalmic compositions. This invention also relates to the use of selective $\beta_2$ adrenergic receptor agonists in the treatment and/or prevention of aforementioned ophthalmic disorders. Alternatively, this invention relates to the use of selective $\beta_2$ adrenergic receptor agonists in the preparation of compositions for the treatment and/or prevention of aforementioned ophthalmic disorders.

Xerophthalmic disorders encompass disorders associated with a decrease in tear secretion level and qualitative aberration in tears can be detected by tear tests known in the art, such as Schirmer's test, cotton thread test, tear film break-up time (BUT), clearance test and lactoferrin measuring test. Examples of diseases accompanied by xerophthalmic disorders include keratoconjunctivitis sicca, such as keratitis superficialis diffusa, superficial punctate keratitis, keratitis filamentosa, etc., lacrimal hyposecretion, xerophthalmia, dry eye, age-related xerophthalmia and Stevens-Johnson syndrome, etc. Improvement of tear secretion can lead to the treatment and/or prevention of these xerophthalmic disorders.

On the other hand, keratoconjunctival disorders encompass disorders associated with injuries that can be detected on the corneal epithelium and/or keratoconjunctiva by fluorescein or rose bengal stains. Examples of diseases accompanied with keratoconjunctival disorders include corneal epithelial disorder, corneal epithelial detachment, keratoconjunctival ulcer, etc. Patients with xerophthalmic disorders often complain of the aforementioned subjective symptoms, but are not always accompanied with keratoconjunctival injuries. However, progress in xerophthalmic disorders often results in complications due to keratoconjunctival disorders. The composition of this invention in its preferred embodiment is effective in treating and/or preventing keratoconjunctival disorders because the composition has an improving action on the concentration of proteins secreted into tears as well as an improving action on tear secretion level. The discovery that stimulation of the $\beta_2$ adrenergic receptor can induce the elevation of protein concentration in tears is a novel aspect of this invention.

In addition, this invention is also useful for wearing a contact lens in the eye. In a state of having a contact lens in, tears optically function as a tear lens. From the physiological point of view, tears play the role of oxygen supplier to the cornea, which is blocked from the atmosphere by the contact lens. Furthermore, to contact lens users, the function of tears as a buffering material, to relieve the incongruous feeling associated with the lens, is also important. With a tear secretion improving agent according to this invention, contact lens wearers can expect an improvement in their contact lens wearing feeling, eyesight correction and such, by promoting tear secretion.

The ophthalmic composition of this invention can be formulated by known methods in the art into eye drops (ophthalmic solutions), injections, eye ointments (ophthalmic ointments), ointments, tablets, capsules, powders, granules, etc., for oral and parenteral administration. Eye drops or eye ointments, which are parenteral preparations, can be not only easily administered but also expected to effect rapidly. With the oral pharmaceutical preparation, a duration of efficacy can be expected.

Alternatively, the composition of this invention can be adsorbed on the surface of contact lens and/or absorbed thereto by soaking. Contact lens constructing such a dosage form can be a lens aiming at correcting the eyesight, or a transparent film serving as a drug carrier. In the latter case, the film can be a soluble one. In such an embodiment, the aforementioned contact lens may be brought into contact with the ocular surface with the hope for the lasting improvement of tear secretion.

The content of a selective $\beta_2$ adrenergic receptor agonist as an active ingredient in each pharmaceutical preparation comprising the composition of this invention can be appropriately altered, corresponding to the method of its administration, etc. For example, eye drops usually contain 0.00001 to 5 w/v %, preferably 0.0001 to 1 w/v % of active ingredient. The pH of eye drops may be in the range acceptable for the general ophthalmic pharmaceutical preparation, specifically adjusted to the range which is favorable for the stability of the active ingredient and less irritating to the ocular-mucous membrane, for example, a pH range of 3 to 9, preferably 5 to 8.5, more preferably 5.5 to 7.5. In addition, the osmotic pressure of eye drops according to this invention is preferred to be less irritating to the ocular-mucous membrane. Specifically, the examples of preferred osmotic pressure are usually about 150 to 450 mOsm, preferably about 260 to 360 mOsm. Alternatively, in terms of the osmotic pressure ratio relative to the physiological saline, it is usually about 0.6 to 2.0, preferably about 0.7 to 1.7, more preferably about 0.8 to 1.5.

The composition of this invention includes eye drops comprising a selective $\beta_2$ adrenergic receptor agonist and buffering agent. Eye drops according to this invention may further contain an isotonizing agent, and may be supplemented with a viscosifying agent and a humectant to retain tears on the ocular surface to keep it moist. Also, to augment the wetness of ocular surface, eye drops may be supplemented with a surfactant and a wetting agent, such as an essential oil or components thereof, etc. Eye drops of this invention can be further formulated into pharmaceutical preparations, as the occasion demands, utilizing a variety of commonly used supplements such as preservatives, stabilizers, antioxidants, pH adjusters, chelating agents, absorption enhancers, etc. which are readily combinable with conventional eye drops.

Buffering agents can be any compounds, provided they can adjust eye drops to the physiological pH; however, they are preferably compounds which exhibit no side effects on the live body at their doses. Examples of buffering agents include borate buffers, citrate buffers, phosphate buffers, tartarate buffers, acetate buffers, carbonate buffers, and amino acid salts, etc.

Isotonizing agents comprise carbohydrates, salts, etc. that are required to give the physiological osmotic pressure to eye drops. Examples of isotonizing agents include carbohydrates such as sorbitol, mannitol, glucose, etc., polyalcohols such as glycerine, propylene glycol, polyethylene glycol, etc., and salts such as sodium chloride, potassium chloride, etc.

Examples of preservatives include quaternary ammonium salts, such as benzalkonium chloride, benzethonium chloride, etc., p-hydroxybenzoic acid esters, such as methyl p-hydroxybenzoate, etc., sorbic acid and salts thereof, chlorobutanol, chlorhexidine gluconate, alkylpolyaminoethylglycine, etc.

Examples of viscosifying agents include hydroxyethylcellulose, hydroxypropylcellulose, methylcellulose, hydroxypropylmethylcellulose, carboxymethylcellulose, carboxyvinyl polymer, polyvinylpyrrolidone, polyvinyl alcohol, hyaluronic acid and salts thereof, etc.

As humectant, for example, carbohydrates and polyalcohols can be used. Examples of carbohydrates are mannitol, dextran, alginic acid (and salts thereof), chondroitin sulfate (and salts thereof), or hyaluronic acid (and salts thereof), etc. Examples of polyalcohols are glycerin, polyethylene glycol or propylene glycol, etc.

A variety of surfactants, which are classified into nonionic, cationic, anionic and amphoteric surfactants and such, can be utilized. Examples of nonionic surfactants include, for example, polyoxyethylenepolyoxypropylene block copolymer, polysorbate, polyoxyethylenesorbitan esters of fatty acids, polyoxyethylene hydrogenated castor oil, etc. Examples of cationic surfactants are POE-POP block-substituted alkylenediamine comprised of alkylenediamines (ethylenediamine, etc.) added with the polyoxyethylene (POE)-polyoxypropylene (POP) block. Anionic surfactants include alkylbenzensulfonic acid and alkylsulfates. In addition, examples of amphoteric surfactants are alkylpolyaminoethylglycine hydrochloride, etc.

As essential oil, peppermint oil, fennel oil, rose oil, bergamot oil, etc. can be used. Examples of essential oil components are menthol, camphor, borneol, etc.

Surfactants, such as polysorbate 80, polyoxyethylene hydrogenated castor oil, etc., water-soluble polymers such as cyclodextrins, polyvinyl pyrrolidone, methylcellulose sodium, hydroxypropylmethylcellulose, methylcellulose, and ethanol, etc., can be used as stabilizers (or solubilizers). Examples of antioxidants are ascorbic acid, sodium ascorbate, tocopherol, sodium thiosulfate, sodium hydrogen sulfite, etc. Examples of chelating agents are sodium edetate (disodium ethylenediamine tetraacetate) sodium citrate, etc. Examples of pH adjusters are hydrochloric acid, citric acid, phosphoric acid, acetic acid, tartaric acid, sodium hydroxide, potassium hydroxide, sodium carbonate, sodium hydrogen carbonate, boric acid, sodium borate, etc.

The composition of this invention includes oral drugs, comprising a selective adrenergic $\beta_2$ receptor agonist, excipient and lubricant. Oral drugs usually contain 0.3 $\mu$g to 300 mg, preferably 30 $\mu$g to 150 mg of a selective adrenergic $\beta_2$ receptor agonist per 1 g of pharmaceutical preparation. Oral drugs can be prepared according to methods that are standard in the art. That is, oral drugs of this invention can be formulated into pharmaceutical preparations by combining a variety of commonly used adjuvants, such as excipients, lubricants, disintegrators, binders, and others, including sweetening agents, flavoring agents, corrigents, adsorbents, preservatives, humectants, antistatic agents, etc. as the occasion demands. Examples of excipients include corn starch, potato starch, sucrose, talc, kaolin, calcium sulfate, calcium carbonate or crystalline cellulose, etc. Examples of lubricants are magnesium stearate, calcium stearate, etc.

As disintegrator, calcium carboxymethylcellulose, low substituted hydroxymethylcellulose, etc. can be used. As binder, hydroxypropylcellulose, hydroxypropylmethylcellulose, polyvinylpyrrolidone, gelatin, cellulose polymers, acrylic acid polymers, methylcellulose, arabic gum, polyvinyl alcohol, etc. can be used.

Doses of the composition of this invention are appropriately selected depending on symptoms, ages, dosage forms, etc. In the case of eye drops, with the instillation of 0.00001 to 5 w/v % eye drops once to several times a day, treatment or preventive effects can be expected. On the other hand, in the case of oral drugs, usual doses of 10 μg to 100 mg a day may be administered once or divided into several portions.

BEST MODE FOR CARRYING OUT THE INVENTION

Test Example 1

Using Japanese albino strain male rabbits, eye drops containing adrenergic β receptor agonists were examined for their tear secretion promoting actions.

1. Preparation of Test Solutions

Prior to use, each adrenergic β receptor agonist was dissolved in a phosphate buffer solution to prepare a 0.1 w/v % solution, which was adjusted to the pH ranging 6.0 to 7.5. Compounds used in this experiment are shown below. The phosphate buffer solution served as control.

Selective Adrenergic $\beta_1$ Receptor Agonist:
  dobutamine hydrochloride (Funakoshi)
Selective Adrenergic $\beta_2$ Receptor Agonists:
  clenbuterol hydrochloride (Sigma),
  fenoterol hydrobromide (Sigma), and
  procaterol hydrochloride (Sigma)

2. Experimental Method

Six rabbits (12 weeks old, weighing 2.0 to 2.5 kg) were used in each group. A test solution (50 μl) was instilled into one eye of the rabbit, and amounts of tears secreted were measured for 5 minutes from 15 to 10 min prior to the instillation of the test solution, for 5 minutes from 5 to 10 min and for 5 minutes from 20 to 25 min after the instillation, three times in total, by the following method. A local anesthetic, 0.4 w/v % oxybuprocaine hydrochloride solution (Santen Pharmaceutical) (50 μl) was instilled into one eye of the rabbit, 5 min later the remaining eye drops and tears were once soaked up using a water absorbing paper, and then a previously weighed filter paper (5×35 mm) was inserted in the lower eyelid area. Five minutes later, the filter paper was recovered, weighed and the increment in weight was taken as the amount of secreted tears. With the amount of secreted tears prior to the instillation of a test solution taken as a basal secretion amount, ratios of increases in the amount of secreted tears to the basal secretion amount were used as the rate of increase in the tear secretion (%).

3. Results

As shown in Table 1, though there were some differences among drugs, the rate of increase in the tear secretion was improved by the instillation of all the selective adrenergic $\beta_2$ receptor agonists tested as compared with that prior to the instillation. On the other hand, the rate of increase in the tear secretion by dobutamine, a selective adrenergic $\beta_1$ receptor agonist, was 8% for 5 minutes from 5 to 10 min after the instillation, and −29% for 5 minutes from 20 to 25 min after that as compared with the basal secretion amount prior to the instillation, showing almost no improvement. With the phosphate buffer solution, almost no improvement was also observed in the rate of increase in the tear secretion. That is, selective adrenergic $\beta_2$ receptor agonists were shown to have an excellent activity to promote tear secretion.

TABLE 1

| | | Rate of increase in tear secretion (*) | |
|---|---|---|---|
| | Drug concentration (w/v %) | For 5 minutes from 5 to 10 min after instillation | For 5 minutes from 20 to 25 min after instillation |
| Dobutamine | 0.1 | 8 | −29 |
| Clenbuterol hydrochloride | 0.1 | 36 | 29 |
| Fenoterol hydrobromide | 0.1 | 144 | 49 |
| Procaterol hydrochloride | 0.1 | 118 | 43 |
| Phosphate buffer solution | — | 9 | 5 |

* %: ratio of increase in the tear secretion as compared with the basal secretion amount.

Test Example 2

Using Japanese albino strain male rabbits, eye drops containing adrenergic β receptor agonists were examined for their actions to promote the tear protein secretion.

1. Preparation of Test Solutions

Prior to use, each adrenergic β receptor agonist was dissolved in a phosphate buffer solution to prepare 0.1 w/v % solution, and adjusted to the pH ranging 6.0 to 7.5. Compounds and compositions of eye drops used in this experiment are shown below using the phosphate buffer solution as control.

Selective Adrenergic $\beta_1$ Receptor Agonist:
  dobutamine hydrochloride (Funakoshi)
Selective Adrenergic $\beta_2$ Receptor Agonists:
  clenbuterol hydrochloride (Sigma),
  fenoterol hydrobromide (Sigma), and
  procaterol hydrochloride (Sigma)

2. Experimental Method

Six rabbits (12 weeks old, weighing 2.0 to 2.5 kg) were used in each group. A test solution (50 μl) was instilled into one eye of the rabbit, and protein concentrations in tears were measured for 5 minutes from 15 to 10 min prior to the instillation of the test solution, for 5 minutes from 5 to 10 min and for 5 minutes from 20 to 25 min after the instillation, three times in total, using the following method. A local anesthetic, 0.4 w/v % oxybuprocaine hydrochloride solution (Santen Pharmaceutical) (50 μl) was instilled into one eye of the rabbit, 5 min later the remaining eye drops and tears were once soaked up using a water absorbing paper, and then a previously weighed filter paper (5×35 mm) was inserted in the lower eyelid area. Five minutes later, the filter paper was recovered, weighed and the increment in weight was taken as the amount of secreted tears. Immediately after measuring the amount of secreted tears, the filter paper thus recovered was placed in a 1.5-ml test tube, 1 ml of the phosphate buffer solution (pH 7.4) was added thereto, and the test tube was stirred for 30 s. After the removal of the filter paper followed by the centrifugation of the solution at 3,000 rpm for 5 min, a stain reagent of Bio-Rad protein assay kit was added to the supernatant to measure the amount of protein and calculate the total amount of protein in the filter paper. From the total amount of protein and that of secreted tears, the protein concentration in tears was calculated.

With the protein concentration in tears prior to the instillation of a test solution taken as a basal protein concentration, ratios of increases in respective protein concentrations relative to the basal protein concentration were used as the rate of increase in protein concentration in tears (%)

3. Results

As shown in Table 2, the rate of increase in protein concentration of tears by 0.1 w/v % procaterol was 76% for 5 minutes from 5 to 10 min after its instillation, and 109% for 5 minutes from 20 to 25 min after that, as compared with the basal secretion amount prior to the instillation, demonstrating the increase in protein concentration in tears. The rates of increase in protein concentration in tears by 0.1 w/v % clenbuterol and 0.1 w/v % fenoterol were both 16% for 5 minutes from 5 to 10 min after their instillations, but elevated to 53% and 43%, respectively, for 5 minutes from 20 to 25 min after the instillations over the basal rate prior to the instillations, showing the increase in protein concentrations. On the other hand, the rate of increase in protein concentration of tears by 0.1 w/v % dobutamine was 9% 5 to 10 min after its instillation, and −19% for 5 minutes from 20 to 25 min after that as compared with the basal protein concentration prior to the instillation with almost no change observed. That is, selective adrenergic $\beta_2$ receptor agonists were confirmed to have an excellent action to promote the protein secretion in tears.

TABLE 2

| | Drug concentration (w/v %) | Rate of increase in tear protein concentration (*) | |
|---|---|---|---|
| | | For 5 minutes from 5 to 10 min after instillation | For 5 minutes from 20 to 25 min after instillation |
| Dobutamine | 0.1 | 9 | −19 |
| Clenbuterol hydrochloride | 0.1 | 16 | 53 |
| Fenoterol hydrobromide | 0.1 | 16 | 43 |
| Procaterol hydrochloride | 0.1 | 76 | 109 |
| Phosphate buffer solution | — | −3 | 4 |

*%: ratio of increase of protein concentration in tears relative to the basal concentration.

Test Example 3

Effects of Systemic Administration

Using Japanese albino strain male rabbits, injections containing selective adrenergic $\beta_2$ receptor agonists were examined for their actions to promote the tear secretion and the protein secretion in tears.

1. Method for Preparing Test Solutions

Prior to use, clenbuterol hydrochloride was dissolved in a physiological saline (concentration 50 μg/ml), and adjusted to the pH in the range 6.0 to 7.5. The physiological saline was used as control.

2. Experimental Method

Six rabbits (11 to 12 weeks old, weighing 2.4 to 2.6 kg) were used in each group. The test solution (50 μg/rabbit) was administered into the ear vein, and amounts of tears secreted were measured 15 to 10 min prior to the administration of the test solution, 5 to 10 min, 20 to 25 min, 40 to 45 min, 60 to 65 min and 120 to 125 min after the administration, six times in total, by the following method. A local anesthetic, 0.4 w/v % oxybuprocaine hydrochloride solution (Santen Pharmaceutical) (50 μl) was instilled into one eye of a rabbit, 5 min later the remaining eye drops and tears were once soaked up using a water absorbing paper, and then a previously weighed filter paper (5×35 mm) was inserted in the lower eyelid area. Five minutes later, the filter paper was recovered, weighed and the increment in weight was taken as the amount of secreted tears. After measuring the amount of secreted tears, the filter paper thus recovered was placed in a 1.5-ml test tube, 1 ml of the phosphate buffer solution (pH 7.4) was added thereto, and the test tube was vortexed for 30 s. After the removal of the filter paper, followed by the centrifugation at 3,000 rpm for 5 min, a stain reagent of Bio-Rad protein assay kit was added to the supernatant to measure the amount of protein and calculate a total amount of protein in the filter paper. From the total amount of protein and that of secreted tears, the protein concentration in tears was calculated. With the amount of secreted tears prior to the administration of a test solution taken as the basal secretion amount, ratios of increases in the secreted tears to the basal secretion amount were used as the rate of increase in the tear secretion (%). In addition, with the protein concentration in tears prior to the administration of a test solution taken as the basal protein concentration, ratios of increases in respective protein concentrations relative to the basal protein concentration were used as the rate of increase in protein concentration in tears (%).

3. Results

As shown in Table 3, by the intravenous administration of clenbuterol, significant increases in the amount of tear secretion as well as the protein concentration in tears were observed. That is, effects of selective adrenergic $\beta_2$ receptor agonist on the improvement of tear secretion were observed also by the systemic administration thereof. These results have suggested that similar effects can be obtained also by the oral administration of the drug.

TABLE 3

| | | Time after administration (min) | | | | |
|---|---|---|---|---|---|---|
| | | 5–10 | 20–25 | 40–45 | 60–65 | 120–125 |
| Clenbuterol hydrochloride | Rate of increase in tear secretion (%) | 155 | 146 | 133 | 68 | 58 |
| | Rate of increase in protein concentration in tears (%) | 139 | 148 | 179 | 188 | 171 |
| Physiological saline | Rate of increase in tear secretion (%) | 6 | 18 | −2 | 11 | −4 |
| | Rate of increase in protein concentration in tears (%) | −3 | 14 | 7 | 20 | 18 |

From the results of test examples 1 to 3, it has been demonstrated that the tear secretion improving agent of this invention has the activities to promote the tear secretion level and to enhance the protein concentration secreted in tears, and that it is useful as a preventive or therapeutic for diseases caused by xerophthalmic and/or keratoconjunctival disorders, with negligible side effects on the heart due to its low pharmacological activities to adrenergic $\beta_1$ receptors.

EXAMPLE 1

Tablets for oral administration were prepared which contained pirbuterol hydrochloride as a selective adrenergic $\beta_2$ receptor agonist.

Corn starch (290 g), crystalline cellulose (500 g), calcium carboxy-methylcellulose (210 g) and pirbuterol hydrochloride (50 g) were mixed, granulated, dried, and pulverized to powders by the standard method. To these powders, an appropriate amount of magnesium stearate was further added and mixed to obtain a powder mixture for compressing, which was compressed to prepare tablets (containing 10 mg/tablet pirbuterol hydrochloride). These tablets are to be administered 1 to 6 tablets/day for a male adult weighing 50 kg.

EXAMPLE 2

Eye drops were prepared which contained fenoterol hydrobromide as a selective adrenergic $\beta_2$ receptor agonist.
Composition of eye drops (in 100 ml):

| | |
|---|---|
| fenoterol hydrobromide | 100 mg |
| sodium chloride | 0.500 g |
| potassium chloride | 0.080 g |
| sodium dihydrogen phosphate | 0.150 g |
| disodium hydrogen phosphate | 0.100 g |
| sodium edetate | 0.005 g |
| 0.1 N sodium hydroxide solution | appropriate amount |
| sterilized pure water | appropriate amount |
| total volume | 100 ml |

Sodium edetate was slowly dissolved in about 80 ml of water. To this solution of sodium edetate were added sodium dihydrogen phosphate and disodium hydrogen phosphate, and dissolved. Next, to this solution, sodium chloride and potassium chloride were added and dissolved. To the resulting solution, fenoterol hydrobromide was added and the solution was adjusted to about pH 6.0 to 7.5 with 0.1 N sodium hydroxide solution, and made to a total volume 100 ml. Eye drops thus prepared were filtered using an 0.2 µm pore cellulose acetate filter, and filled up into a sterilized plastic container. Eye drops are instilled 1 to 3 drops every time and 3 to 6 times a day.

EXAMPLE 3

Eye drops were prepared which contained salbutamol sulfate as a selective adrenergic $\beta_2$ receptor agonist.
Composition of eye drops (in 100 ml):

| | |
|---|---|
| salbutamol sulfate | 100 mg |
| sodium chloride | 0.500 g |
| potassium chloride | 0.080 g |
| sodium dihydrogen phosphate | 0.150 g |
| disodium hydrogen phosphate | 0.100 g |
| sodium edetate | 0.005 g |
| 0.1 N sodium hydroxide solution | appropriate amount |
| sterilized pure water | appropriate amount |
| total volume | 100 ml |

Eye drops are prepared in a similar manner as described in Example 2, and instilled 1 to 3 drops every time and 3 to 6 times a day.

EXAMPLE 4

Eye drops were prepared which contained procaterol hydrochloride as a selective adrenergic $\beta_2$ receptor agonist.

Composition of eye drops (in 100 ml):

| | |
|---|---|
| procaterol hydrochloride | 10 mg |
| sodium chloride | 0.700 g |
| potassium chloride | 0.100 g |
| boric acid | 1.000 g |
| sodium borate | 0.200 g |
| sodium edetate | 0.050 g |
| 0.1 N sodium hydroxide solution | appropriate amount |
| sterilized pure water | appropriate amount |
| total volume | 100 ml |

Sodium edetate was slowly dissolved in about 80 ml of water. To this solution of sodium edetate were added boric acid and sodium borate, and dissolved. Next, to this solution, sodium chloride and potassium chloride were added and dissolved. To the resulting solution was then added procaterol hydrochloride, and the solution was adjusted to about pH 6.0 to 7.5 with 0.1 N sodium hydroxide solution, and made to a total volume 100 ml. Eye drops thus prepared were filtered using an 0.2 µm pore cellulose acetate filter, and filled up into a sterilized plastic container. Eye drops are instilled 1 to 3 drops every time and 3 to 6 times a day.

EXAMPLE 5

Eye drops were prepared which contained pirbuterol hydrochloride as a selective adrenergic $\beta_2$ receptor agonist.

Composition of eye drops (in 100 ml):

| | |
|---|---|
| pirbuterol hydrochloride | 10 mg |
| sodium chloride | 0.700 g |
| potassium chloride | 0.100 g |
| boric acid | 1.000 g |
| sodium borate | 0.200 g |
| sodium edetate | 0.050 g |
| 0.1 N sodium hydroxide solution | appropriate amount |
| sterilized pure water | appropriate amount |
| total volume | 100 ml |

Eye drops are prepared in a similar manner as described in Example 4, and instilled 1 to 3 drops every time and 3 to 6 times a day.

EXAMPLE 6

Eye drops were prepared which contained clenbuterol hydrochloride as a selective adrenergic $\beta_2$ receptor agonist. Composition of eye drops (in 100 ml):

| | |
|---|---|
| clenbuterol hydrochloride | 1 mg |
| sodium chloride | 0.500 g |
| potassium chloride | 0.080 g |
| sodium dihydrogen phosphate | 0.150 g |
| disodium hydrogen phosphate | 0.100 g |
| sodium edetate | 0.005 g |
| 0.1 N sodium hydroxide solution | appropriate amount |
| sterilized pure water | appropriate amount |
| total volume | 100 ml |

Eye drops are prepared in a similar manner as described in Example 2, and instilled 1 to 3 drops every time and 3 to 6 times a day.

Industrial Applicability

By the present invention, an ophthalmic composition with negligible side effects on the heart has been provided. The composition of this invention is excellent in promoting not only tear secretion level but also protein secretion into tears. Since the proteins in tears comprise ingredients participating in the maintenance and repair of corneal functions, the composition of this invention is useful for the treatment and prevention of a variety of ophthalmic disorders.

The composition of this invention can be applied to, for example, preventives or therapeutics for diseases associated with xerophthalmic and keratoconjunctival disorders.

What is claimed is:

1. A method for improving tear secretion, said method comprising administering to a subject in need of an improvement in tear secretion one or more compounds selected from the group consisting of (a) clenbuterol, (b) fenoterol, (c) salbutamol, (d) salmeterol, (e) hexoprenaline, (f) pirbuterol, (g) mabuterol, (h) bambuterol, (i) formoterol, (j) meluadrine, (k) tulobuterol, (l) levosalbutamol, and (m) salts of (a)–(l).

2. The method of claim 1, wherein said improvement in tear secretion comprises an increased tear secretion level or an increased protein concentration in tears.

3. The method of claim 1, wherein the administration is parenteral.

4. The method of claim 3, wherein the administration is by instillation in the eye.

5. The method of claim 1, wherein the administration is oral.

* * * * *